US011610667B2

(12) United States Patent
Gurson et al.

(10) Patent No.: US 11,610,667 B2
(45) Date of Patent: Mar. 21, 2023

(54) SYSTEM AND METHOD FOR AUTOMATED ANNOTATION OF RADIOLOGY FINDINGS

(71) Applicant: RAD AI, Inc., Berkeley, CA (US)

(72) Inventors: Doktor Gurson, Berkeley, CA (US); Jeffrey Chang, Berkeley, CA (US); Jeffrey Snell, Berkeley, CA (US); Eric Purdy, Berkeley, CA (US); Brandon Duderstadt, Berkeley, CA (US); Deeptanshu Jha, Berkeley, CA (US)

(73) Assignee: RAD AI, INC., Berkeley, CA (US)

( * ) Notice: Subject to any disclaimer, the term of this patent is extended or adjusted under 35 U.S.C. 154(b) by 97 days.

(21) Appl. No.: 16/688,623

(22) Filed: Nov. 19, 2019

(65) Prior Publication Data
US 2020/0160982 A1 May 21, 2020

Related U.S. Application Data

(60) Provisional application No. 62/769,131, filed on Nov. 19, 2018.

(51) Int. Cl.
G16H 30/40 (2018.01)
G16H 30/20 (2018.01)
G06N 3/08 (2023.01)

(52) U.S. Cl.
CPC ........... G16H 30/40 (2018.01); G06N 3/08 (2013.01); G16H 30/20 (2018.01)

(58) Field of Classification Search
None
See application file for complete search history.

(56) References Cited

U.S. PATENT DOCUMENTS

| 10,127,662 | B1 * | 11/2018 | Reicher | G06T 7/30 |
| 10,140,421 | B1 | 11/2018 | Bernard et al. | |
| 2013/0290031 | A1 | 10/2013 | Kay et al. | |
| 2014/0379378 | A1 | 12/2014 | Cohen-Solal et al. | |
| 2015/0112725 | A1 | 4/2015 | Ryan | |
| 2015/0348229 | A1 * | 12/2015 | Aguirre-Valencia | G06T 3/60 345/419 |
| 2018/0060533 | A1 * | 3/2018 | Reicher | G16H 15/00 |
| 2018/0330828 | A1 | 11/2018 | Hayter | |

(Continued)

FOREIGN PATENT DOCUMENTS

| WO | WO-0239415 A2 * | 5/2002 | ............ A61B 5/044 |
| WO | 2019025601 A1 | 2/2019 | |

OTHER PUBLICATIONS

Dai, N., Liang, J., Qiu, X., & Huang, X. (2019). Style transformer: Unpaired text style transfer without disentangled latent representation. Ithaca: Cornell University Library, arXiv.org. (Year: 2019).

(Continued)

Primary Examiner — Lena Najarian
(74) Attorney, Agent, or Firm — Jeffrey Schox; Caitlin Ploch

(57) ABSTRACT

A method for the automated annotation of radiology findings includes: receiving a set of inputs, determining a set of outputs based on the set of inputs, assigning labels to the set of inputs, and annotating the set of inputs based on the labels. Additionally, the method can include any or all of: presenting annotated inputs to a user, comparing multiple sets of inputs, transmitting a set of outputs to a radiologist report, or any other suitable processes.

16 Claims, 8 Drawing Sheets

(56) References Cited

U.S. PATENT DOCUMENTS

| | | | |
|---|---|---|---|
| 2019/0021677 A1* | 1/2019 | Grbic | A61B 5/7292 |
| 2019/0122073 A1* | 4/2019 | Ozdemir | A61B 6/5217 |
| 2019/0139218 A1 | 5/2019 | Song et al. | |
| 2020/0334416 A1 | 10/2020 | Vianu et al. | |
| 2020/0342967 A1 | 10/2020 | Bronkalla et al. | |
| 2021/0090694 A1 | 3/2021 | Colley et al. | |
| 2021/0110912 A1 | 4/2021 | Mukherjee | |
| 2021/0327596 A1 | 10/2021 | Tahmasebi Maraghoosh et al. | |

OTHER PUBLICATIONS

Ebesu, T. A. (2019). Deep learning for recommender systems (Order No. 13900137). Available from ProQuest Dissertations & Theses Global. (2293976827). (Year: 2019).

Garud, H. D. (2019). Transforming human pose forecasting (Order No. 27814956). Available from ProQuest Dissertations & Theses Global. (2399247743). (Year: 2019).

Jettakul, A., Wichadakul, D., & Vateekul, P. (2019). Relation extraction between bacteria and biotopes from biomedical texts with X attention mechanisms and domain-specific contextual representations. BMC Bioinformatics, 20, 1-17.

Koncel-Kedziorski, R. (2019). Understanding and generating multi-sentence texts (Order No. 13814316). Available from ProQuest Dissertations & Theses Global. (2305944561). (Year: 2019).

Nandhakumar et al. Clinically Significant Information Extraction from Radiology Reports. Jan. 31-Aug. 20, 2017 (Aug. 31, 2017).

Sanjabi, N. (Apr. 2018). Abstractive text summarization with attention-based mechanism (Projecte Final de Master Oficial). UPC, Facultat d'Informatica de Barcelona. (Year: 2018).

Sanjabi, N. (Apr. 2018). Abstractive text summarization with attention-based mechanism (Projecte Final de Master Oficial). UPC, Facultat d'Informatica de Barcelona. (Year: 2018).

Song, H. (2018). Data-driven representation learning in multimodal feature fusion (Order No. 10838232). Available from ProQuest Dissertations & Theses Global. (2094858110). (Year: 2018).

Zech et al. Natural Language-based Machine Learning Models for the Annotation of Clinical 1-20 Radiology Reports. Jan. 30, 2018 (Jan. 30, 2018).

Zhang et al. Learning to Summarize Radiology Findings. Oct. 8, 2018 (Oct. 8, 2018). 1-20 [retrieved on Nov. 18, 2020].

Xue, Y., et al., "Multimodal Recurrent Model with Attention for Automated Radiology Report Generation", Medical Image Computing and Computer Assisted Intervention—MICCAI 2018. MICCAI 2018. Lecture Notes in Computer Science, vol. 11070. Springer, Cham. https://doi.org/10.1007/978-3-030-00928-1_52 (Year: 2018).

Lou, Robert, et al., "Automated detection of radiology reports that require u follow-up imaging using natural language processing feature engineering and machine learning classification", Journal of digital imaging, 33(1), 131-136. (Year: 2020).

\* cited by examiner

Time = $t_0$

Time = $t_1$

//* # SYSTEM AND METHOD FOR AUTOMATED ANNOTATION OF RADIOLOGY FINDINGS

CROSS-REFERENCE TO RELATED APPLICATIONS

This application claims the benefit of U.S. Provisional Application No. 62/769,131, filed 19 Nov. 2018, which is incorporated in its entirety by this reference.

TECHNICAL FIELD

This invention relates generally to the radiology field, and more specifically to a new and useful system and method for the automated annotation of radiology findings in the radiology field.

BACKGROUND

Current radiology workflows have several limitations. First, the general workflow is a relatively long and inefficient process, requiring a large number of interactions with and/or inputs from the radiologist. A large number of actions (which herein refer to any or all of mouse clicks, mouse hovers, hotkey presses, mouse click and hotkey, mouse hover and hotkey, other button presses, or any other interaction(s)), for instance, are typically required as the radiologist views and analyzes a series of images at a radiology workstation computer.

Furthermore, current radiology workflows result in a large number of inconsistencies (e.g., inter-radiologist inconsistencies, intra-radiologist inconsistencies, etc.), due to non-standardized processes for taking measurements of findings. This makes it difficult, for instance, to compare findings and measurements between prior and current studies as well as those taken by different radiologists.

Thus, there is a need in the radiology field for an efficient, accurate, and consistent system and method for the assessment of patient findings in a radiology workflow.

DESCRIPTION OF THE PREFERRED EMBODIMENTS

The following description of the preferred embodiments of the invention is not intended to limit the invention to these preferred embodiments, but rather to enable any person skilled in the art to make and use this invention.

1. Overview

Figure 1:
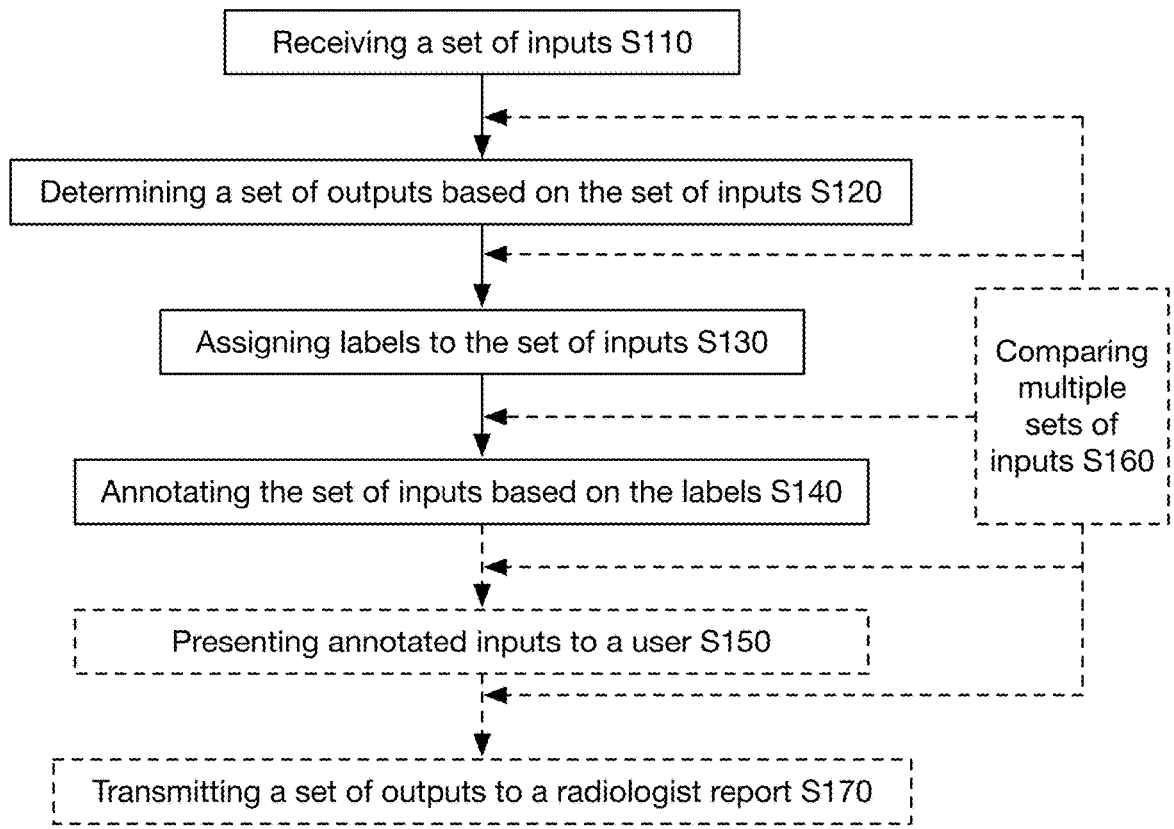
FIG. 1 is schematic representation of the method.

As shown in FIG. 1, an embodiment of a method 100 for automated annotation of radiology findings includes: receiving a set of inputs S110, determining a set of outputs based on the set of inputs S120, assigning labels to the set of inputs S130, and annotating the set of inputs based on the labels S140. Additionally, the method 100 can include any or all of: presenting annotated inputs to a user S150, comparing multiple sets of inputs S160, transmitting a set of outputs to a radiologist report S170, or any other suitable step(s).

2. Benefits

The system and method for automated processing in a radiology workflow can confer several benefits over the current systems and methods used in radiology workflows.

First, in some variations, the system and/or method can confer the benefit of achieving comparable results (e.g., outputs, findings, measurements, etc.) between studies, based on the establishment of a consistent analysis process. In some examples, for instance, the method—through consistent analysis algorithms—enables results to be accurately compared between a prior and a current study for the same patient. Additionally or alternatively, the method can enable results to be accurately compared between different patients.

Second, in some variations, the system and/or method can confer the benefit of establishing an intuitive interface through which radiologists or other healthcare personnel can quickly and thoroughly assess medical findings.

In some examples, for instance, the method can minimize a number of actions (e.g., mouse clicks, keyboard clicks, hotkey clicks, etc.) required by a radiologist during part or all of a conventional radiology workflow. In a set of specific examples, abnormal findings are displayed to a radiologist (e.g., at a PACS workstation) with zero clicks and normal findings are displayed with one action (e.g., mouse click, hover, etc.).

In some examples, the method links two or more studies together, such that the two or more studies can be viewed together (e.g., side-by-side), processed together, manipulated together (e.g., scrolling through images of one study initiates scrolling through corresponding images of the second study), or otherwise associated.

In some examples, the method confers the benefit of automatically displaying abnormal findings, which can function to bring important findings to immediate attention, decrease time to intervention, or perform any other suitable function. Additionally or alternatively, the method can require one or more clicks to display normal findings, thereby making all information accessible but only automatically displaying the most important results (e.g., to minimize crowding of annotations on a display, reduce time to intervention, etc.).

Third, in some variations, the method functions to integrate with and display annotations to radiologists in accordance with a variety of radiology groups and associated software platforms (e.g., PACS). In some examples, for instance, images are received from a radiology information system (RIS) prior to being sent to a PACS, wherein the images are annotated at a remote server and the annotations (e.g., in the form of a DICOM overlay) are sent back to the RIS (and subsequently getting passed to a PACS).

Additionally or alternatively, the system and method described below can confer any other suitable benefit over conventional methods.

3. Method

The method 100 for automated annotation of radiology findings is preferably performed during and integrated within a traditional radiology workflow. As such, the processes involved in the method 100 and any associated system can include and/or be configured to interface with the workflow, software, associated hardware, protocols, or other components of any or all of the following: a Picture Archiving and Communication System (PACS) and/or alternative image viewing and image storage platform, a voice and/or speech recognition platform, a Radiology Information System (RIS) and/or alternative patient tracking platform, an electronic medical record (EMR) database, an electronic health record (EHR) database, a Clinical Information System (CIS) platform and/or alternative management software, a smart worklist, one or more vendor-neutral archive (VNA) components, or any other suitable components.

In some variations, at least part of the method 100 is configured to be performed between the PACS display portion and the voice recognition system portion of a standard radiology workflow. Additionally or alternatively, the method 100 can be performed between any other steps of a traditional radiology workflow, outside of a radiology workflow, in place of a radiology workflow, or otherwise performed.

The method 100 can be performed in compliance with one or more patient privacy programs (e.g., Health Insurance Portability and Accountability Act (HIPAA), General Data Protection Regulations (GDPR), etc.) or any other suitable programs. In some variations, for instance, patient information (e.g., patient identifiers, patient-sensitive information, etc.) is de-identified (e.g., encrypted) during the method and then re-identified (e.g., decrypted) once the inputs have been processed (e.g., partially processed, fully processed, etc.).

3.1 Method—Receiving a Set of Inputs S110

The method includes receiving a set of inputs S110 associated with a patient, which functions to prompt the subsequent processes of the method 100. The inputs can include any or all of: a set of one or more images, a series, and/or a study from an imaging modality (e.g., radiography/x-ray, computed tomography (CT), magnetic resonance imaging (MRI), ultrasound, positron emission tomography (PET)/CT, other forms of nuclear medicine, mammography, digital breast tomosynthesis, PET/MRI, etc.); images from one or more procedures (e.g., procedures involving fluoroscopy, molecular imaging, mammography, etc.); video data (e.g., kinetics action data, video data of blood vessels, etc.), patient information (e.g., patient metadata, demographic information, etc.); patient condition information (e.g., predicted medical condition, previous medical condition, patient history, etc.); and/or any other suitable information.

Figure 4:
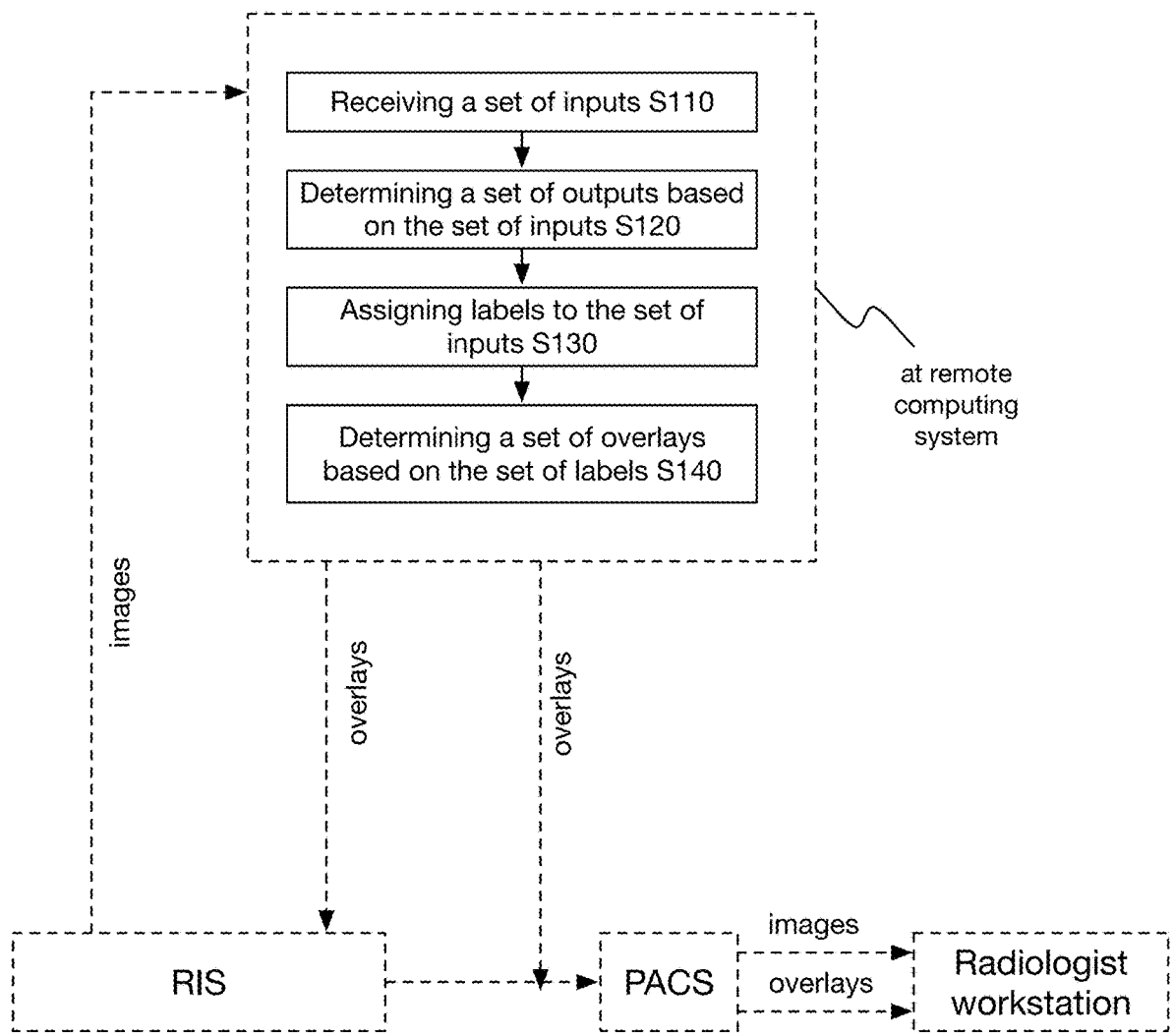
FIG. 4 depicts a schematic representation of a variation of the method.
Figure 5:
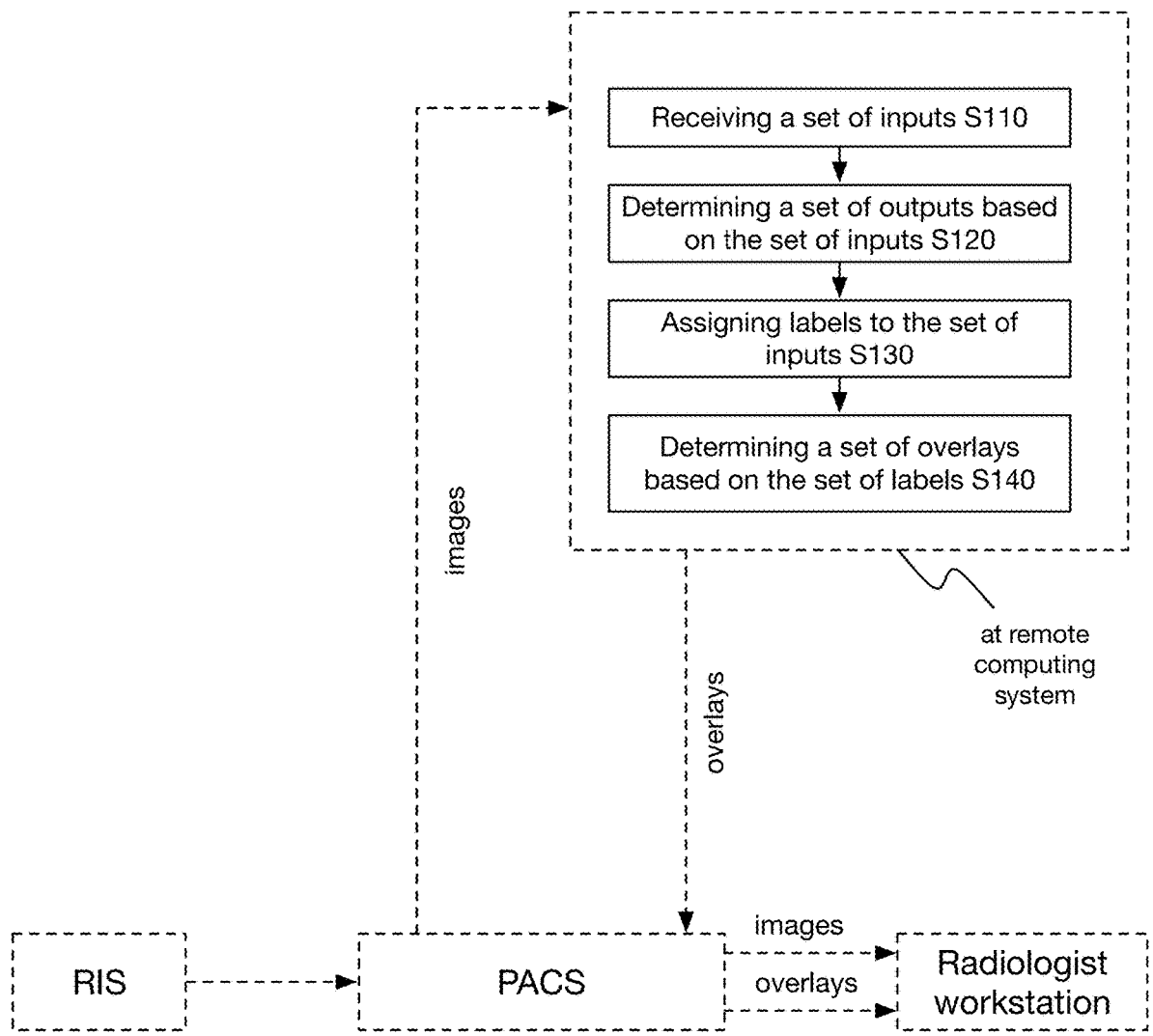
FIG. 5 depicts a schematic representation of a variation of the method.

The set of inputs (e.g., instances, series, studies, etc.) are preferably received from an imaging modality (e.g., CT scanner, MRI scanner, etc.), such as from a RIS associated with the imaging modality (e.g., as shown in FIG. 4), a PACS associated with the imaging modality (e.g., as shown in FIG. 5), a combined RIS/PACS associated with the imaging modality, and/or any other suitable source. Additionally or alternatively, inputs (e.g., patient information, health records, etc.) can be received through an alternative server or database (e.g., local server at healthcare facility, remote server, cloud-based storage, etc.), an EMR database, an EHR database, or any other suitable software or storage.

S110 can additionally include applying any number of pre-processing steps to the inputs, such as, but not limited to: compression (e.g., image compression, lossless compression, etc.), cropping, labeling (e.g., labeling one or more images with metadata), rotation (e.g., flipping), or any other suitable process. In some variations involving cross-sectional imaging (e.g., axial cross-sectional imaging), S110 includes flipping or otherwise rotating a set of images received from a RIS and transmitting the properly rotated images back to the RIS. The images can then optionally be transmitted to any or all of: a remote server for further processing (e.g., to perform the remaining processes of the method), a PACS, and/or any other suitable endpoint(s).

In a first set of variations, the set of inputs includes a set of axial cross-sectional (e.g., perpendicular to a main axis of the human body, etc.) images (equivalently referred to herein as "slices") associated with one or more anatomical regions of the patient. In examples, for instance, the set of inputs includes a set of cross-sectional images of a region of the patient's body (e.g., brain) taken from any or all of: MRI, PET, SPECT, CT, and/or any other imaging modality.

Figure 6:
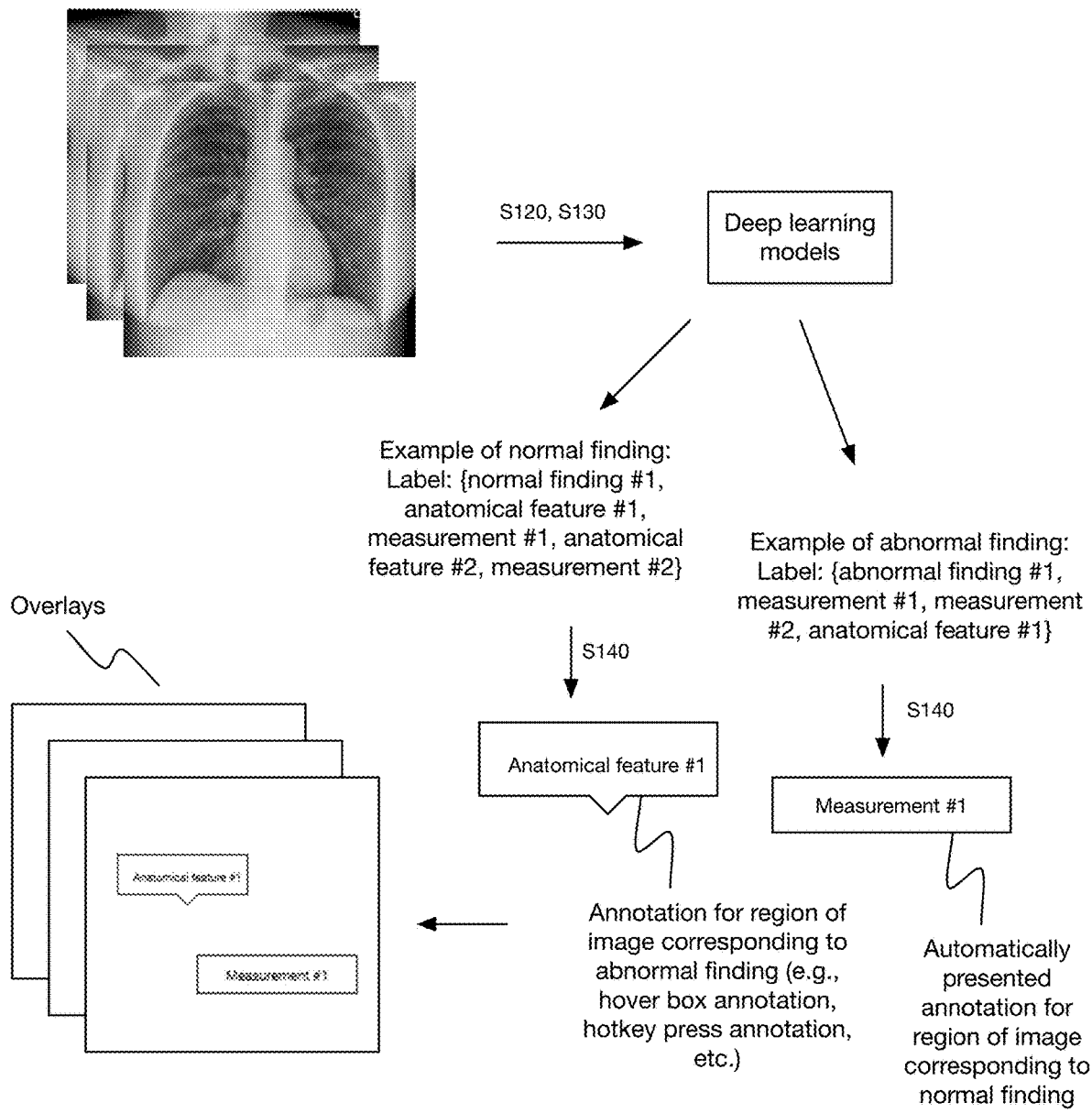
FIG. 6 depicts a variation of the method.

In a second set of variations (e.g., as shown in FIG. 6), the set of inputs includes non-axial cross-sectional images associated with one or more anatomical regions of the patient, such as those taken from radiography, fluoroscopy, angiography, and/or any other imaging modalities. In examples, for instance, the set of inputs includes any or all of: non-axial images (e.g., of a patient's blood vessels), video data (e.g., kinetics action data, video data of a patient's blood vessels, etc.), and/or any other suitable inputs. In a specific example, the set of inputs includes image data from a chest radiograph.

3.2 Method—Determining a Set of Outputs Based on the Set of Inputs S120

The method 100 includes determining a set of outputs based on the set of inputs S120, which functions to assess the state (e.g., condition, health, etc.) of the patient.

The set of outputs preferably includes one or more medical findings, herein referred to as findings, which conventionally refer to something of note or otherwise worth mentioning in a study. The majority of findings are in the form of a measurement or otherwise associated with a measurement, but not all findings require or have an associated measurement. Each finding can preferably be categorized as either an abnormal finding or a normal finding; additionally or alternatively, a finding can be included in multiple categories, a separate category, any number of sub-categories, be un-categorized, or otherwise characterized.

Abnormal findings can include any or all of: uncharacteristic or unexpected features (e.g., unexpected anatomical feature, etc.), such as those uncharacteristic in size (e.g., smaller, larger, etc.), volume, material composition (e.g., density, stiffness, tissue composition, etc.), shape (e.g., irregular outline, symmetric, asymmetric, etc.), location, or any other features. Additionally or alternatively, abnormal findings can include any or all of: disease states (e.g., presence of mass, tumor, etc.), medical indications, illnesses, irregularities (e.g., anatomical irregularities), or other suitable features. Further additionally or alternatively, abnormal findings can include pertinent negatives and/or pertinent positives.

Normal findings include characteristic and/or or expected features (e.g., anatomical feature characteristic in size, location, composition, etc.). In some variations, the normal findings include an identification of anatomical features, such as basic anatomy (e.g., heart, brain, head and neck, stomach, etc.), detailed anatomy (e.g., specific muscle, specific rib, particular vascular structure, etc.), or any other suitable types or groupings of anatomical features. Additionally or alternatively, normal findings can include pertinent negatives and/or pertinent positives. In some variations, the set of normal findings includes all findings other than abnormal findings; alternatively, these categories can overlap.

The set of outputs can additionally or alternatively include any number of measurements, which refer to quantitative and/or qualitative parameters associated with (e.g., determined based on) one or more findings. Additionally or alternatively, a measurement can be associated with and/or determined based on any or all of: a type of scanner or imaging modality, a predicted or pre-established medical condition, metadata associated with one or more inputs, patient information, or any other suitable feature(s).

A sub-set of possible measurements are those which characterize a size (e.g., linear dimension, length, width, height, thickness, volume, surface area, etc.) of a finding. These measurements can include any or all of: single axis measurements (e.g., short axis length, long axis length, intermediate axis length, an averaged axis length, etc.); multi-axis measurements (e.g., shortest and longest axis lengths); representative region of interest (ROI) circles or ellipses (e.g., for determination of maximum standard uptake value (SUV) on PET/CT, for determination of average Hounsfield unit (HU) on CT as with adrenal nodules (for adenoma confirmation) or any variety of cysts, for reporting whether maximum SUV in an entire organ or region is within the normal range on PET/CT, etc.); an estimated volume for a volumetric structure or anatomy; a segmentation of one or more anatomical features and any results determined from the segmentation; an estimated amount and/or percentage of a material (e.g., total fat, visceral fat and subcutaneous fat as determined from evaluating an entire study and adjusted for the entire body according to tested and verified population statistics and/or demographics, etc.); or any other size characterization(s).

Additionally or alternatively, the set of measurements can characterize a location of a finding (e.g., a particular brain lobe corresponding to a tumor, a particular rib corresponding to a fracture, etc.).

Further additionally or alternatively, the set of measurements can include one or more predictive measurements. In a specific example, for instance, a measurement can be in the form of a percentage risk of malignancy for a lesion (e.g., determined based on one or more algorithms having undergone analytical and/or clinical testing). In variations having predictive measurements, the inputs of the method 100 can further include any information (e.g., outside information, aggregated information, patient-specific information) necessary to determine the value of the predictive measurement, such as any or all of: publications (e.g., academic publications), clinical study results, medical databases, predictive algorithms, or any other suitable information source. In some examples, for instance, a predictive measurement is determined based on a current measurement (e.g., tumor short axis length) and a predictive algorithm (e.g., for tumor growth based on the results of a clinical study).

Predictive measurements can include any or all of: predictive parameters (e.g., predictive sizes, locations, etc.), percentage likelihoods of the occurrence of a particular disease state or condition, predicted time points at which a particular disease state or condition may occur or progress to a predetermined severity, or any other suitable predictive quantities. In one example, for instance, a set of predictive measurements are associated with a set of abnormal findings (e.g., 70% chance of pancreatitis vs. 25% chance of underlying duodenitis, 4% chance of an underlying pancreatic head mass causing obstruction, etc.). In another example, a predictive measurement is found corresponding to a predicted location (e.g., with a percentage likelihood above a predetermined threshold) of a bowel perforation.

Determining the set of measurements preferably includes both determining the type of measurement to take (e.g., short axis measurement, volumetric measurement, predictive measurement, etc.) and determining a value of the measurement. Additionally or alternatively, determining the set of measurements can include just one of these steps and/or any additional steps.

S120 is performed, at least in part, through the processing of the set of inputs with a set of one or more models, which in turn at least partially produces the set of outputs (e.g., abnormal findings, normal findings, measurements, etc.). The set of models preferably includes one or more convolutional neural networks (e.g., V-nets, U-nets, hybrid 3D/2D ConvNets, two-stream inflated 3D ConvNet (I3D), neural networks conventionally used in video processing and motion, etc.), but can additionally or alternatively include any suitable algorithms (e.g., deep learning algorithms), neural networks (e.g., other than convolutional neural networks (CNNs)), or any other suitable models. The models can be trained through supervised learning (e.g., based on annotated image data), trained through unsupervised learning, untrained, or otherwise determined.

Additionally or alternatively, determining the set of outputs can include any or all of: referencing a lookup table (e.g., to associate a finding with the result(s) of one or more models, to associate a finding with either a normal label or an abnormal label, to determine a subsequent set of models to be applied, etc.); comparing one or more results with a previous result associated with the patient (e.g., a finding from a prior study, a set of images from a prior study, etc.), comparing a set of findings or other results with each other (e.g., in order to rank a severity of a set of findings, in order to determine a finding associated with a set of comorbidities, etc.), and/or any other suitable process(es).

In some variations, the set of models includes a set of convolutional neural networks (e.g., V-nets) applied to a set of voxels making up a study (e.g., set of image slices from an imaging modality), or any other suitable set of inputs. Additionally or alternatively, the set of models can include a set of U-nets applied to a set of pixels in one or more inputs (e.g., study, series, single image, etc.), or any other suitable model (e.g., algorithm) applied to any suitable base unit (e.g., pixel, voxel, prescribed region or data subset, segmentation, etc.) of an input (e.g., image, set of images, patient information, etc.) or set of inputs.

The set of models can be applied in series, in parallel, or in a combination of parallel and series. In some variations, the models are grouped into a first set and a second set, wherein the first set of models are each applied in parallel; after this parallel processing, a second set of models are initiated and applied, each of these models in the second set also applied in parallel. Additionally or alternatively, all models can be applied in parallel together, all applied in series, otherwise applied, and/or otherwise grouped.

In some variations, the result of a model (e.g., CNN, V-net, etc.) or set of models can inform the selection of one or more subsequent models (e.g., subsequent CNN, subsequent V-nets). In some examples, for instance, a first model results in the determination of a particular anatomy or anatomical region; based on this determination, a set of models are selected which correspond to possible findings associated with that particular anatomy or anatomical region. In a specific example, a first set of models (e.g., V-nets corresponding to a set of possible anatomical regions) are applied to a study, resulting in a determination that the images in the study are those of a heart. Based on this determination, a second set of models are selected (e.g., based on a lookup table) which correspond to potential findings (e.g., normal findings, abnormal findings, ventricular aneurysm, aortic stenosis, mitral stenosis, etc.) that can occur in the heart. The results of this second set of models (e.g., applied in parallel, applied in series, etc.) can include any or all of: a normal finding, an abnormal finding, a measurement corresponding to a finding, or any other suitable output.

Selecting a subsequent set of models can involve any or all of: referencing a lookup table or database (e.g., stored in remote storage, stored in local storage, etc.), processing with one or more models or algorithms, receiving an input from a user (e.g., verification from a radiologist), looking at a set of results (e.g., findings, measurements, etc.) collectively (e.g., to determine if they may be comorbidities for another condition or finding, etc.), or any other suitable process. Alternatively, the same set of models can be automatically applied to every input.

S120 is preferably performed at a remote computing system (e.g., cloud-based server) but can additionally or alternatively be partially or fully performed at a local computing system (e.g., healthcare facility server). S120 is preferably performed after S110 but can additionally or alternatively be performed multiple times throughout the method, or at any other suitable time.

In a first variation of S120, wherein the set of inputs includes a set of axial cross-sectional images (e.g., taken from an MRI scanner, taken from a CT scanner, etc.), the set of outputs is determined based on a set of CNN models, wherein the set of CNN models includes at least one of a U-net and a V-net, and the set of outputs includes any or all of: a set of normal findings, a set of abnormal findings, location information and associated measurements (e.g., location/position of an anatomical feature), orientation information and associated measurements (e.g., orientation angle of an anatomical feature), size information and associated measurements (e.g., size of an anatomical feature, size of a pathology, change in size of an anatomical feature and/or pathology, etc.), characterization of the state of an anatomical feature (e.g., healthy diseased, broken, characterization based on a contrast value/pixel value/voxel value of the anatomical feature, based on a detected fracture or break, etc.), and/or any other suitable outputs. Additionally or alternatively, the set of inputs can be otherwise processed (e.g., with a non-convolutional neural network, with any suitable deep learning model, etc.), and the set of outputs can include any other suitable information.

In a second variation of S120, wherein the set of inputs includes a set of non-axial cross-sectional images (e.g., taken from a chest radiograph), the set of outputs is determined based on a set of trained deep learning models, and the set of outputs includes any or all of: a set of normal findings, a set of abnormal findings, location information and associated measurements (e.g., location/position of an anatomical feature), orientation information and associated measurements (e.g., orientation angle of an anatomical feature), size information and associated measurements (e.g., size of an anatomical feature, size of a pathology, change in size of an anatomical feature and/or pathology, etc.), characterization of the state of an anatomical feature (e.g., healthy diseased, broken, characterization based on a contrast value/pixel value/voxel value of the anatomical feature, based on a detected fracture or break, etc.), and/or any other suitable outputs. Additionally or alternatively, the set of inputs can be otherwise processed (e.g., with a CNN, with any suitable deep learning model, etc.), and the set of outputs can include any other suitable information.

In a specific example of the second variation, a set of images from a chest radiograph is processed with a set of trained deep learning models (e.g., trained through supervised learning, trained through unsupervised learning, etc.) to determine a set of outputs, such as any or all of: radial tube position, identification of the location of a set of anatomical features, a nodule size, and/or any other suitable outputs.

Additionally or alternatively, axial cross-sectional images can be processed according to the second variation (e.g., with trained deep learning models), non-axial cross-sectional images can be processed according to the first variation (e.g., with V-nets, with U-nets, etc.), and/or any suitable images can be processed in any suitable way.

3.3 Assigning Labels to the Set of Inputs S130

The method 100 includes assigning labels (alternatively referred to as classes) to the set of inputs S130 based on the set of outputs, which functions to assign the information found in the outputs to the corresponding/relevant parts (e.g., anatomic region) of the inputs.

Assigning labels to the set of inputs S130 preferably includes assigning findings and their corresponding measurements to each of the corresponding base units (e.g., pixels, voxels, etc.) of the input(s). Additionally or alternatively, the labels can include any other suitable outputs, a reference to other base units and/or inputs (e.g., reference to a separate voxel having the same finding, reference to another pixel forming a measurement such as a short axis, reference to a previous study corresponding to the same pertinent negative, etc.), or any other suitable class.

Any or all of the labels can be binary, such as those indicating: the presence or absence of a finding (e.g., predicted or determined disease state, mass, tumor, occluded vessel, cyst, stone, etc.), the categorization of a finding as either a normal finding or an abnormal finding, the categorization of a finding as either a pertinent negative or a pertinent positive, the relation of one finding to another finding (e.g., when the findings are comorbidities), or any other indication. Additionally or alternatively, one or more of the labels can correspond to a value on a spectrum or continuum, such as the value of a measurement corresponding to a finding (e.g., short axis length of a mass).

Further additionally or alternatively, labels can correspond to attributes (e.g., image attributes), descriptors, a comparison between a previous study and a current study (e.g., percentage increase in tumor diameter), a predictive finding or measurement, patient information (e.g., patient demographic information), imaging information (e.g., type of imaging modality, type of scan, contrast level, anatomical region being imaged, etc.), healthcare facility information (e.g., site of scan), and/or any other suitable feature of the set of inputs.

In some variations, the labels are determined, ranked, weighted, or otherwise processed based on conditions associated with their relative importance. These conditions are preferably predetermined (e.g., preset, determined based on a lookup table, etc.), but can additionally or alternatively be dynamically determined (e.g., based on a model, based on other dynamically determined labels such as labels associated with other findings, etc.), continuously updated, updated at predetermined intervals of time, or otherwise determined.

Additionally or alternatively, the labels can include a reference to other parts of the input data (e.g., other image slices in a study, other voxels in the same image, etc.) or other inputs (e.g., patient information associated with a finding in the image). In some variations, for instance, a label associated with a voxel in a first image refers to one or more other images which have a similarly labeled voxel (e.g., to group a set of images indicating the presence of a necrotic mass).

A base unit (e.g., voxel, pixel, region, image, study, etc.) of the input can include multiple labels determined through the application of multiple models (e.g., multiple V-nets, multiple hybrid 3D/2D ConvNets, etc.). Additionally or alternatively, each base unit can include a single label, no label, multiple labels determined by a single model, or any other type and designation of labels.

S130 is preferably performed at a remote computing system (e.g., cloud computing system, remote server, etc.), further preferably the same remote computing system as used previously in the method (e.g., in S120); additionally or alternatively, part or all of S130 can be performed locally (e.g., on healthcare facility premises, on local server of healthcare facility, etc.). The remote computing system preferably communicates with a RIS, but can additionally or alternatively communicate with a PACS, an EMR database, an EHR database, a local server of a healthcare facility, a remote server of a healthcare facility, and/or any other suitable systems.

S130 is preferably performed after S120 (e.g., once findings and measurements have been determined), but can additionally or alternatively be performed during S120 (e.g., after the application of each model, after the application of one or more models, after the application of the first set of models, etc.), at multiple times throughout the method, or at any other suitable time(s) during the method.

S130 can additionally include any number of processing steps, such as compressing an input (e.g., prior to labeling, after labeling, etc.), cropping, or any other process(es). S130 can further additionally include storing the labels (e.g., at the remote computing system, at a RIS, at a PACS, at an EMR database, at an EHR database, etc.) and/or any other data (e.g., the associated images, findings associated with the labels, etc.).

In one variation, S130 includes determining a set of labels for a set of base units (e.g., pixels, voxels, etc.) of a set of cross-sectional images (e.g., axial cross-sectional images), wherein the set of labels is determined based on processing the set of images with a set of CNNs (e.g., V-nets, U-nets, etc.), and wherein the labels specify any or all of: one or more findings and whether they are normal or abnormal; a set of measurements associated with the set of findings; and/or any other suitable information (e.g., patient information, healthcare facility information, etc.). In a specific example of this variation, S130 includes determining, for each of the base units, a label identifying an anatomic region (e.g., based on a segmentation process of a CNN), a label identifying each of a set of normal findings if applicable (e.g., in combination with the anatomic region), a label identifying each of a set of abnormal findings if applicable (e.g., in combination with the anatomic region), and/or any other suitable labels.

In a second variation, S130 includes determining a set of labels for a set of base units (e.g., pixels, voxels, images, etc.) of a set of non-axial cross-sectional images (e.g., coronal/frontal cross-sectional images, sagittal/longitudinal cross-sectional images, etc.), wherein the set of labels is determined based on processing the set of images with a set of trained deep learning models, and wherein the labels specify any or all of the information in the first variation.

3.4 Method—Annotating the Set of Inputs Based on the Labels S140

The method 100 includes annotating the set of inputs based on the labels, which functions to prepare the set of inputs for viewing (e.g., quick viewing, viewing with a minimal number of actions, viewing with a minimal number of clicks, etc.) by a radiologist or other user (e.g., in a radiology workflow, outside of a radiology workflow, etc.).

An annotation refers to an indicator for a radiologist to view (e.g., on a PACS, at a PACS viewer, at a radiologist workstation, etc.) or otherwise perceive each annotation corresponding to one or more outputs as reflected in the labels. In some variations, the annotation is in the form of a hover box, which can be viewed, for instance, at or near a mouse cursor on a display (e.g., monitor at a radiologist workstation). The hover box can include any or all of: text (e.g., reciting a particular finding, reciting the value of a measurement, etc.), an image (e.g., a simplified symbol corresponding to a finding, a simplified symbol corresponding to an anatomic region, etc.), a link (e.g., to a relevant prior study, to a corresponding image in the same study, web link, etc.), or any other suitable information. Additionally or alternatively, annotations can include stationary boxes (e.g., text boxes); any number of location indicators, such as, but not limited to: arrows (e.g., pointing to a particular anatomy), lines (e.g., separating anatomical features), circles (e.g., encircling a region corresponding to an abnormal finding); images; and/or any other suitable indicator(s). In a specific example, for instance, a combination of hover boxes and arrows are used to locate and specify each rib in a scan of a patient's torso. The annotation location on the input is preferably chosen to clearly and quickly indicate the region of interest as well as to minimize crowding and/or blockage of important regions; additionally or alternatively, the annotation location can be chosen in any suitable way.

In some variations, a feature of an annotation (e.g., color, size, duration for which it appears, etc.) can be determined and/or adjusted based on any or all of: the severity of a finding, the importance of a finding, the novelty of a finding, the value of a measurement (e.g., to indicate that a value is within a normal range, to indicate that a value is outside of a normal range, etc.), its relationship to another annotation (e.g., to a comorbidity finding), or any other suitable parameter.

In preferred variations, annotations are chosen to have minimal components (e.g., only visual components) in order to minimize the time and effort required by the radiologist to interpret the annotation. However, in some variations, in addition or alternative to visual components (e.g., text in a hover box), annotations can include auditory components (e.g., auditory alerts, alarms, speech, etc.), tactile components, or any other suitable component(s).

In some variations, an annotation type (e.g., hover box, arrow, etc.) and/or annotation feature (e.g., color, size, duration, etc.) depend on the finding type (abnormal finding versus normal finding). In specific examples, for instance, the base units (e.g., voxels) of an input corresponding to a normal finding are annotated with a first type of annotation (e.g., hover box), whereas base units corresponding to (e.g., including, locating, etc.) an abnormal finding are annotated with a second type of annotation (e.g., arrow). In alternative variations, base units corresponding to a normal finding are exempt from an annotation, base units corresponding to all findings are annotated in the same way, or annotations can be determined and/or assigned in any other suitable way.

S140 is preferably performed at a remote computing system, further preferably after the labels in S130 have been determined and assigned to the corresponding base units. Additionally or alternatively, any or all of S140 can be performed at a local computing system, S140 can be performed during a previous process (e.g., as outputs are determined during S120, as labels are assigned during S130, etc.), S140 can be performed multiple times throughout the method 100, or S140 can be performed at any other suitable time during the method.

S140 preferably includes producing an overlay, further preferably a DICOM overlay, based on the set of annotations, wherein the overlay is presented to a radiologist (or other viewer) with the set of images and functions to present annotations of the overlay at appropriate regions (e.g., base units) of the images. The overlay further preferably functions to prescribe a set of actions (e.g., hovering, click, hotkey press, etc.) required to display any or all of the annotations. Additionally or alternatively, the overlay can function to enable a set of annotations to be stored and/or perform any other suitable function.

The overlay is preferably produced in accordance with and based on a particular radiology group and its software platform, which refers to the radiology group's software suite (e.g., speech-to-text software, DICOM image viewer software, etc.) and optionally the associated application programming interfaces (APIs). This functions to enable the overlays to be properly displayed to the radiologist or other viewer, such as at a workstation associated with a PACS viewer. In some variations, the overlay can be an additional overlay to others produced for a PACS viewer. In other variations, data associated with the overlay is integrated into a separate overlay.

The overlays can optionally be sent to a RIS, which can function to reduce or eliminate the need for complex integration required to interface with a PACS. In some variations, for instance, input images to the method 100 are received from a RIS and the overlays are sent back to the RIS, where the RIS would transmit and optionally adjust the images and overlays together based on a predetermined protocol. Additionally or alternatively, the overlays can be sent directly to a PACS and/or to any other suitable endpoints.

There is preferably at least one overlay produced for each image. Additionally or alternatively, a smaller number of overlays with respect to the number of images can be produced (e.g., wherein overlays are only produced for images having abnormal findings, wherein overlays are only produced for images having normal and/or abnormal findings, etc.), multiple overlays can be produced for a single image (e.g., wherein separate overlays are produced for normal findings vs. abnormal findings, wherein each overlay is associated with a particular action required to display the information of the overlay, etc.), and/or any suitable number of overlays can be produced. In a first variation, a single overlay is produced for each image, which includes all of the annotations. In a second variation, multiple overlays are produced for each image, wherein each overlay includes the annotations that require the same action to display to the user. In a specific example, for instance, a first overlay includes all annotations (e.g., abnormal findings) which are automatically displayed to the viewer and a second overlay includes all annotations which require a specific action (e.g., hover, click, etc.) to display to the viewer.

S140 can optionally include storing any or all of the overlays, such as at one or more of: remote storage associated with a remote computing system (e.g., a remote computing system described previously); storage (e.g., remote storage, local storage, etc.) associated with the healthcare facility at which the imaging is performed, such as any or all of an EMR database, an EHR database, and PACS storage; and/or at any other suitable location.

Additionally or alternatively, S140 can include transforming data from the overlays into other information, such as text to be integrated into a radiologist report and/or saved in a patient's medical record). In a specific example, data from the overlays is used to auto fill one or more sections of a radiologist's report (e.g., findings section).

In one variation, S140 includes producing an overlay for each of a set of images, wherein the overlay includes a set of annotations corresponding to normal findings and a set of annotations corresponding to abnormal findings (if present), along with any associated measurements if determined. In a specific example, a DICOM overlay is produced for each image, which is transmitted to one or both of a RIS and a PACS, wherein the DICOM overlays are displayed with the images while being viewed (e.g., at a PACS viewer) by a radiologist.

3.5 Method—Presenting Annotated Inputs to a User S150

The method 100 can optionally include presenting the annotated inputs to a radiologist or other user, such as a radiologist workstation (e.g., PACS viewer, monitor, user device, etc.).

S150 can include any or all of: toggling the display of annotations (e.g., annotations including or in the form of: measurements, ROI circles, ellipses or bounding boxes, arrows, numbering, informational text, heat maps, etc.) when holding a hotkey, toggling the display of annotations on and off with a hotkey, or otherwise triggering or controlling the display of annotations. Annotations can be displayed as part of a PACS- or DICOM-compatible overlay, superimposed with a separate program, or otherwise displayed.

The way in which annotations are displayed (e.g., type of trigger, displayed automatically versus displayed in response to a trigger, duration of display, whether or not to display corresponding annotations among subsequent images, type of annotation, etc.) preferably depends on one or more labels, such as a label specifying the type of finding (e.g., abnormal finding versus normal finding). This can be integrated within the overlay, transmitted to a viewer (e.g., PACS viewer) and/or to another system (e.g., RIS) as a set of control commands, integrated within the viewer itself, or otherwise configured to enable the annotations to be displayed properly, if at all. In preferred variations, the way in which annotations are displayed is configured to bring radiologist attention to the most important outputs (e.g., abnormal finding measurements) as quickly and as easily as possible. This can involve any or all of: removing or minimizing a number of actions (e.g., clicks, hovers, hotkeys, etc.) required to display an abnormal finding annotation; requiring more actions to display a normal finding annotation as compared to an abnormal finding annotation; configuring (e.g., programming, hard coding, etc.) an abnormal finding annotation to have a longer duration than a normal finding annotation; configuring an abnormal finding annotation to be more noticeable (e.g., bigger in size, more brightly colored, animated, etc.) than a normal finding annotation; and/or otherwise differentiating the way in which abnormal finding annotations and normal finding annotations are displayed. Additionally or alternatively, the way in which annotations are displayed can depend on a type of label (e.g., measurement versus name of finding). In some variations, for instance, annotations with findings can be automatically displayed whereas annotations with measurements require an action (e.g., click, click+hotkey) to be displayed.

Figure 3A:
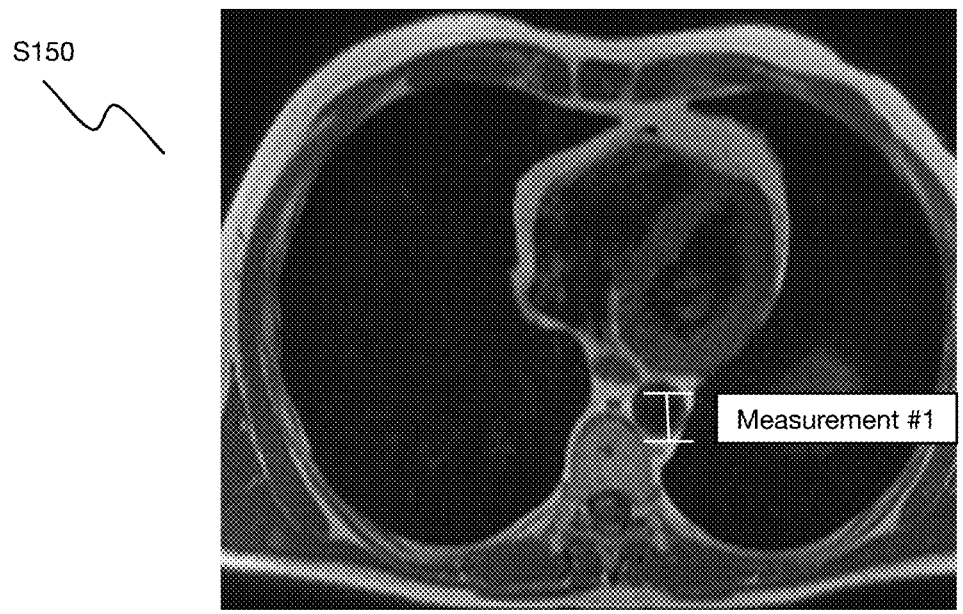
FIGS. 3A-3B depict a variation of a set of outputs of the method.
Figure 3B:
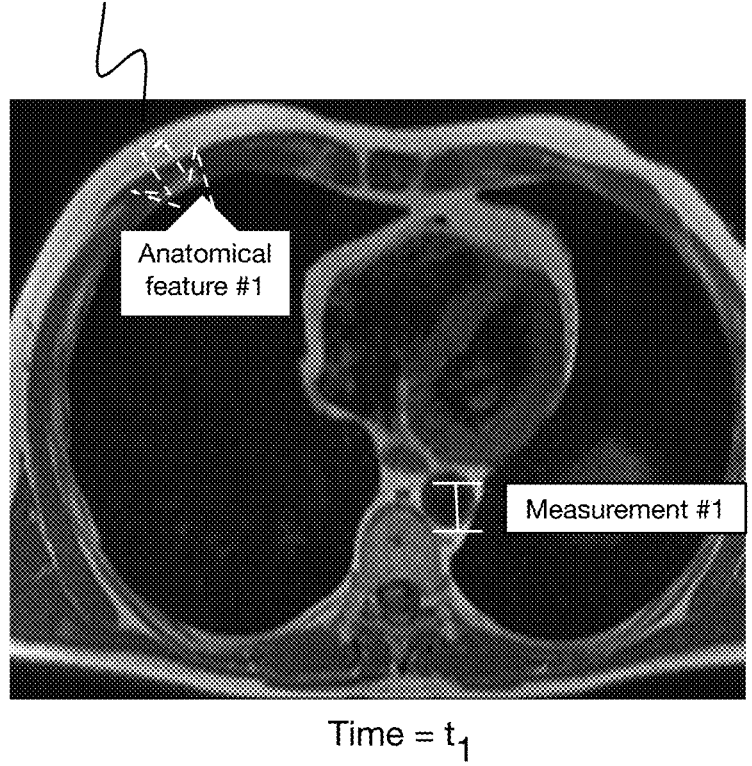

In preferred variations (e.g., as shown in FIGS. 3A-3B), annotations corresponding to abnormal findings (e.g., arrow and text box containing a measurement of an abnormal finding) are displayed automatically upon the presentation of inputs (e.g., images in a study) to a radiologist (e.g., at a radiologist workstation, on a PACS viewer), whereas annotations corresponding to normal findings (e.g., hover boxes indicating an anatomical feature) are only displayed in response to a trigger (e.g., radiologist hovering over corresponding area with mouse cursor).

In a specific example, abnormal finding measurements are displayed automatically.

In preferred variations, the annotations that are automatically presented to the radiologist are configured to minimize the time and effort required for interpretation; as such, the annotations can be configured to look identical to those conventionally (e.g., manually) made by radiologists. Alternatively, annotations can be presented in any other suitable way.

Additionally or alternatively, the continuity of annotation display among multiple parts of one or more inputs (e.g., among multiple images in a single study, among multiple images in multiple studies, etc.) is determined, at least in part, by the label; in examples, for instance, annotations corresponding to abnormal findings are displayed on all relevant images (e.g., images containing this finding), whereas annotations corresponding to normal findings are only displayed on the image for which the trigger (e.g., hover) was applied.

Further additionally or alternatively, the duration of an annotation can depend on the type of annotation. In specific examples, for instance, annotations corresponding to abnormal findings are constantly displayed (e.g., unless turned off by a user), whereas annotations corresponding normal findings (e.g., hover box with measurement of a normal finding) are displayed briefly (e.g., less than 10 seconds, while a user hovers over that area, etc.).

Additionally or alternatively, the way in which annotations are displayed can depend on preferences and/or actions of a particular radiologist, radiology group, healthcare facility, or other suitable entity. In a specific example, for instance, annotations selected (e.g., clicked, pinned, highlighted, etc.) by the radiologist on a first image (e.g., slice) of a study can be automatically displayed for the corresponding feature (e.g., image feature, anatomical region, anatomical region corresponding to a normal finding, etc.) in a second image from the same study.

In alternative variations, the way in which annotations are displayed can be independent of the content of the annotations (e.g., labels corresponding to a finding). In some variations, for instance, all annotations are displayed automatically to minimize and/or eliminate all actions (e.g., clicks) from a radiologist. Alternatively, annotations can be displayed only upon prompting or in any other suitable way.

In some variations, the radiologist can make an otherwise transient annotation into a permanent annotation. In a set of specific examples in which annotations corresponding to normal findings are only transiently displayed (e.g., removed after a predetermined time has passed, removed after a predetermined time has passed since an action such as a hover, etc.), the radiologist can perform an action (e.g., click, shift+click, pressing a hotkey, double click, etc.) to make the annotation permanently displayed.

In some variations, the method additionally includes providing a list of findings (e.g., all findings, abnormal findings, normal findings, etc.) and the corresponding images for which annotations corresponding to the findings have been added.

3.6 Method—Comparing Multiple Sets of Inputs S160

The method can optionally include comparing multiple sets of inputs S160, which can function to: monitor patient progress between different time points (e.g., between a prior and a current study), determine consistent and comparable measurements between inputs (e.g., measurements determined through consistent algorithms and models), or perform any other suitable function.

Figure 7A:
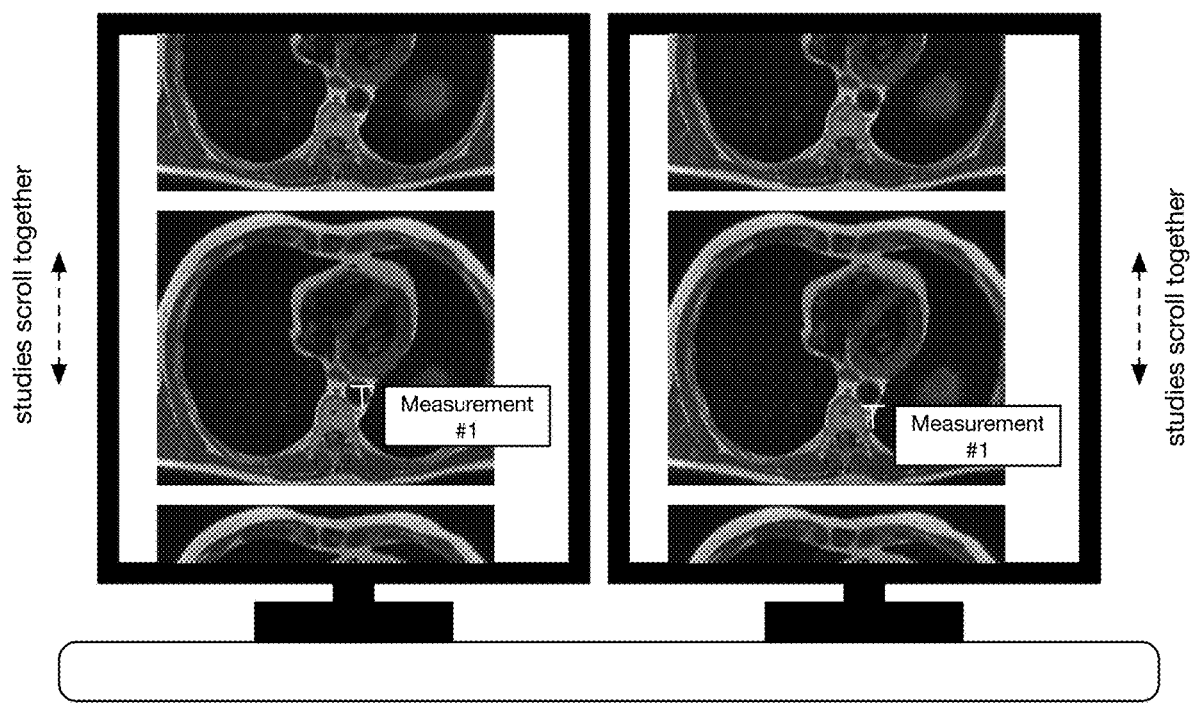
FIGS. 7A-7B depict a variation of a display of one or more outputs of the method.
Figure 7B:
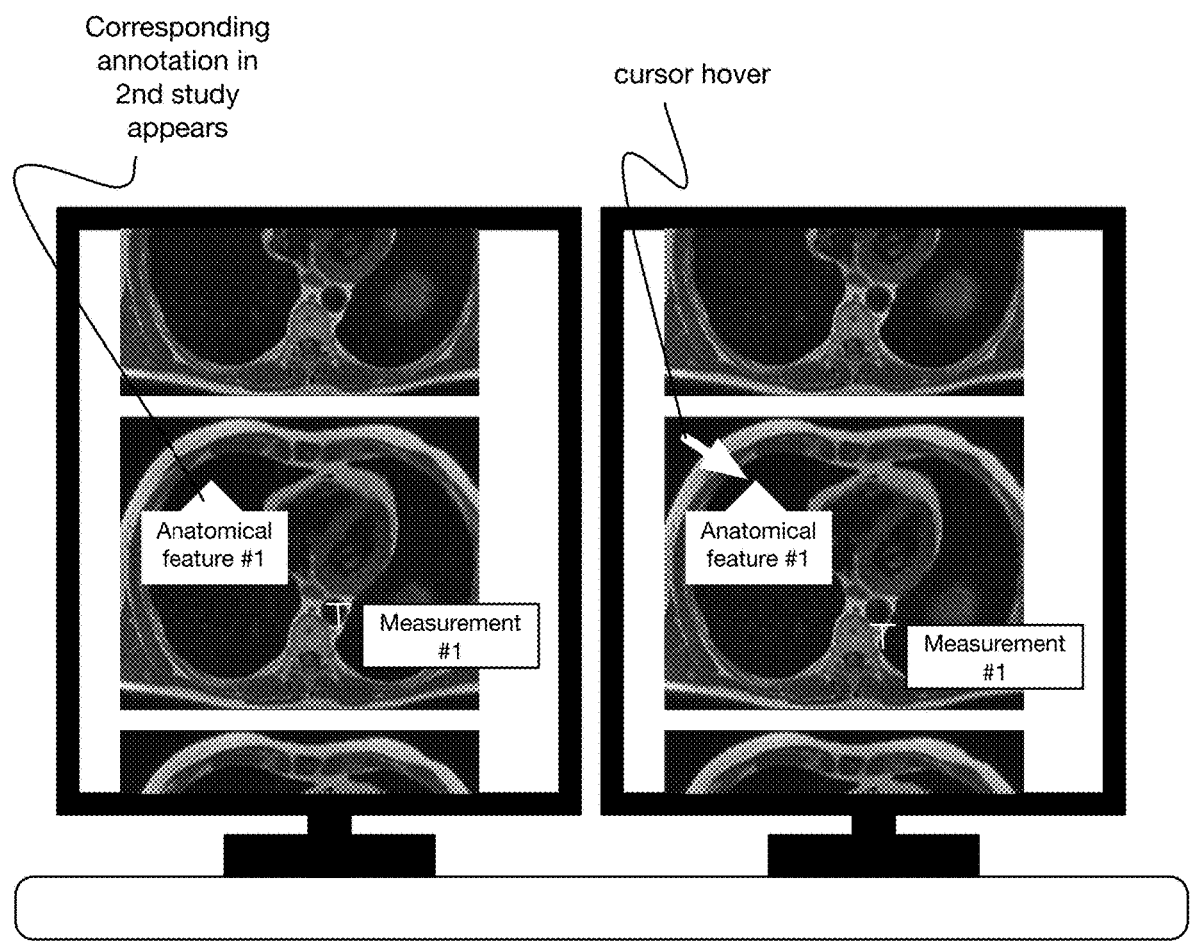

S160 can involve any or all of: pre-registration and/or magnification level matching (e.g., using reference anatomy appearing in both studies) of multiple studies (e.g., multiple studies of a single patient having: a common finding, shared set of labels, common imaging modality, etc.); linkage of one or more prior exams with a hotkey and/or mouse click in PACS; automatic side-by-side viewing of multiple studies at a PACS viewer or other display at a radiologist workstation (e.g., as shown in FIGS. 7A-7B); automatic scrolling of a first study (e.g., prior study) upon scrolling of a second (e.g., current) study (e.g., as shown in FIG. 7A); and/or any other suitable process.

In a specific example, for instance, S160 involves registration of every prior study for the same patient on the same modality (e.g., imaging modality, scanner, etc.), the registration including one or both of: matching the most similar anatomic slices on cross-sectional imaging (e.g., CT, PET/CT, MRI, etc.) and matching the same degree of zoom and order of images on single images. Preferably, as the radiologist scrolls through the current study, the prior study automatically begins scrolling together with the current study starting from the most closely matching anatomic slice (e.g., as shown in FIG. 7A). The images can be scrolled together and/or otherwise manipulated or arranged in any suitable way (e.g., in accordance with any suitable radiology viewer), such as through any or all of: vertical scrolling (e.g., as shown in FIG. 7A), horizontal scrolling, scrolling among a stacked set of images, and/or any other suitable scrolling. Further preferably, any actions (e.g., hotkeys, clicks, hovering, etc.) performed on one study can initiate a corresponding response on the other study (e.g., as shown in FIG. 7B). An action (e.g., hover) which results in a hover box showing a normal finding on the current study, for instance, can prompt a hover box showing the corresponding normal finding in the prior study (e.g., as shown in FIG. 7B).

S160 can be performed at any time during the method and can be initiated automatically or in response to any suitable trigger (e.g., initiated by radiologist, based on scan type, based on finding of a study, etc.). In some variations, multiple sets of images are registered in response to a first set of inputs being received in S110; alternatively, images in first and second studies can be registered after the images in the first study have been annotated in S140, or at any other time(s) throughout the method. In a first example, S160 is performed as the first set of inputs are received in S110, thereby enabling the second set of inputs to be processed in parallel with the first set. In a second example, a first and second set of inputs are registered in response to determining the presence of an abnormal finding (e.g., labeling an abnormal finding) in the first set. In a third example, any or all of S160 is performed at the discretion and prompting of a radiologist. Alternatively, S160 can be performed at any other time and in any suitable way.

3.7 Method—Transmitting a Set of Outputs to a Radiologist Report S170

The method can additionally or alternatively include transmitting any or all of the set of outputs to a radiologist report S170, which can function to: minimize or eliminate interactions between a radiologist and a voice recognition platform (through which radiologists conventionally report findings for a radiologist report), increase the accuracy and/or uniformity of radiologist reports, and/or perform any other suitable function. S170 preferably involves the automatic insertion of radiologist-appropriate finding and/or comparison text into a report within the voice recognition platform, which can be initiated, for instance, with a hotkey and/or click. Alternatively, S170 can be performed in absence of a voice recognition platform.

In some variations, abnormal findings and any corresponding measurements are integrated into a radiologist report upon prompting (e.g., hotkey and click) by a radiologist, wherein the abnormal findings and measurements, in conjunction with any additional information received at a voice recognition platform, are dictated into a radiologist report.

S170 is preferably performed after annotated inputs have been presented to a user S150, but can additionally or alternatively be performed prior to S150, in lieu of S150, or at any other time(s) during the method.

3.8 Method—Variations

Figure 2:
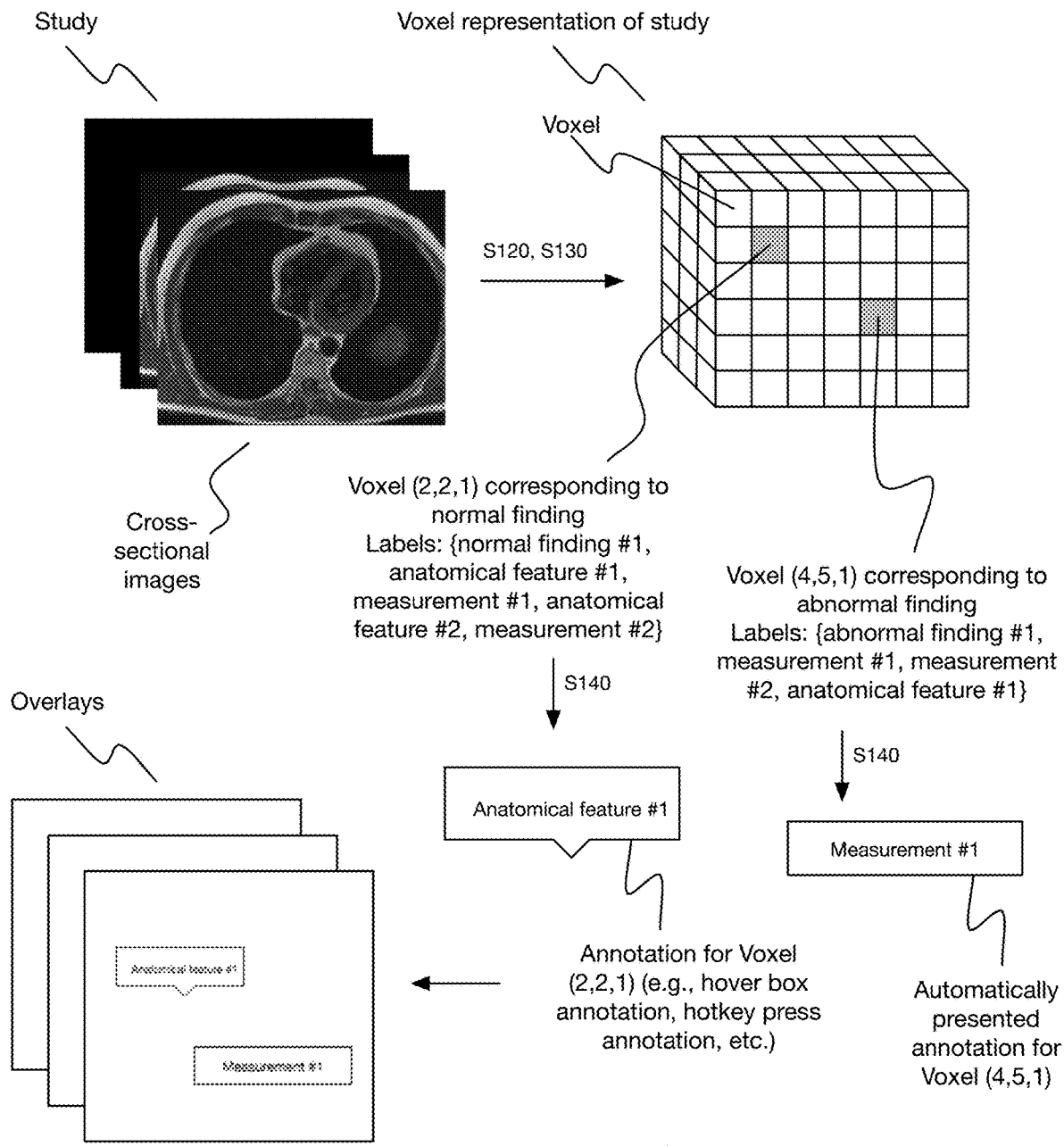
FIG. 2 depicts a variation of the method.

In a first variation of the method 100 (e.g., as shown in FIG. 2), the method includes: receiving a study (set of image slices) from an imaging modality (e.g., MRI scanner); representing the study as a set of voxels; processing each of the voxels with a set of CNNs (e.g., V-nets, U-nets, hybrid 3D/2D ConvNets, I3Ds, etc.) to determine a set of outputs corresponding to the voxels; labeling each of the voxels based on these corresponding outputs; determining a set of annotations based on (e.g., that include) the outputs; producing a set of overlays (e.g., DICOM overlays) including the set of annotations; and presenting the outputs to a radiologist viewing the study through the overlays, wherein determining how and if to present the annotations to the radiologist is determined based on one or more labels associated with the annotations. Additionally or alternatively, the method can include automatically pulling up a prior study and analyzing in parallel, presenting outputs of both studies to the radiologist, and/or any other suitable steps.

In a second variation of the method 100 (e.g., as shown in FIG. 6), the method includes: receiving a study (set of image slices) from an imaging modality (e.g., chest radiograph); processing the images with a set of trained deep learning models to determine a set of outputs corresponding to the set of images; labeling each of the voxels based on these corresponding outputs; determining a set of annotations based on (e.g., that include) the outputs; producing a set of overlays (e.g., DICOM overlays) including the set of annotations; and presenting the outputs to a radiologist viewing the study through the overlays, wherein determining how and if to present the annotations to the radiologist is determined based on one or more labels associated with the annotations. Additionally or alternatively, the method can include automatically pulling up a prior study and analyzing in parallel, presenting outputs of both studies to the radiologist, and/or any other suitable steps.

Although omitted for conciseness, the preferred embodiments include every combination and permutation of the various method steps and various system components.

As a person skilled in the art will recognize from the previous detailed description and from the figures and claims, modifications and changes can be made to the preferred embodiments of the invention without departing from the scope of this invention defined in the following claims.

We claim:

1. A method for automatically annotating a set of radiology images, the method comprising:

receiving, at a remote computing system, a set of Digital Imaging and Communications in Medicine (DICOM) images, wherein the set of DICOM images is associated with a patient;

processing the set of DICOM images, comprising:
with a first convolutional neural network (CNN), the CNN comprising at least one of a V-net and a U-net, determining an anatomical feature associated with the set of DICOM images;
based on the anatomical feature and with a lookup table, determining a second CNN, the second CNN comprising at least one of a V-net and a U-net;
with the second CNN:
determining a set of abnormal findings associated with the set of DICOM images; and
determining a set of normal findings associated with the set of DICOM images;

assigning a set of labels to the set of DICOM images, wherein the set of labels is determined based on the set of abnormal findings and the set of normal findings;

automatically determining a set of annotations based on the set of labels, wherein the set of annotations comprises:
a first subset of annotations, wherein the first subset of annotations is associated with the set of abnormal findings; and
a second subset of annotations, wherein the second subset of annotations is associated with the set of normal findings;

producing a set of DICOM overlays associated with the set of DICOM images and comprising the set of annotations;

automatically displaying, at a display of a radiology workstation, the set of DICOM images and the set of DICOM overlays, wherein:
each of the first subset of annotations is displayed automatically upon display of an associated DICOM image; and
each of the second subset of annotations is displayed in an event that a user hovers a cursor proximal to an annotation of the second subset of annotations and for a duration of time while the user hovers the cursor proximal to the annotation of the second subset of annotations;

in response to detecting a hotkey press from the user while the annotation of the second subset of annotations is displayed, increasing the duration of time such that the annotation of the second subset of annotations is displayed throughout an entire remaining duration of display of the associated DICOM image;

contemporaneously and automatically with displaying the set of DICOM images, displaying a second set of DICOM images associated with the patient, wherein the second set of DICOM images is recorded prior to the set of DICOM images, and wherein the second set of DICOM images is automatically processed in parallel with the set of DICOM images to determine a second set of annotations.

2. The method of claim 1, wherein each of the second set of DICOM images is linked with a corresponding image of the set of DICOM images, wherein scrolling between images of the set of DICOM images triggers a scrolling between corresponding images of the second set of DICOM images.

3. The method of claim 2, further comprising, in the event that the user hovers the cursor proximal to the annotation of the second subset of annotations, displaying a corresponding annotation associated with the second set of DICOM images.

4. The method of claim 1, further comprising preprocessing any or all of the set of DICOM images, wherein preprocessing any or all of the set of DICOM images comprises rotating one or more images.

5. The method of claim 1, further comprising automatically filling in at least a portion of a radiologist report based on the set of DICOM overlays.

6. The method of claim 5, wherein the portion comprises a findings section.

7. The method of claim 1, wherein the set of DICOM images is received from a Radiology Information System (RIS).

8. The method of claim 1, wherein the set of DICOM images is received from a Picture Archiving and Communication System (PACS).

9. A method for automatically annotating a set of radiology images, the method comprising:
receiving, at a remote computing system, a set of radiology images;
with a first set of deep learning models, determining an anatomical feature associated with the set of radiology images;
based on the anatomical feature and with a lookup table, determining a second set of deep learning models;
with the second set of deep learning models:
determining a set of abnormal findings associated with the set of radiology images; and
determining a set of normal findings associated with the set of radiology images;
assigning a set of labels to the set of radiology images, wherein the set of labels is determined based on the set of abnormal findings and the set of normal findings;
determining a set of annotations based on the set of labels, wherein the set of annotations comprises:
a first subset of annotations; and
a second subset of annotations;
producing a set of image overlays associated with the set of radiology images and comprising the set of annotations;
displaying, at a display of a radiology workstation, the set of radiology images and the set of image overlays, wherein:
each of the first subset of annotations is displayed automatically upon display of an associated radiology image and throughout an entire duration of display of the associated radiology image; and
each of the second subset of annotations is displayed in an event that a user hovers a cursor proximal to an annotation of the second subset of annotations and for a duration of time while the user hovers the cursor proximal to the annotation of the second subset of annotations; and
in response to detecting a hotkey press from the user while the annotation of the second subset of annotations is displayed, increasing the duration of time such that the annotation of the second subset of annotations is displayed throughout an entire remaining duration of display of the associated radiology image.

10. The method of claim 9, wherein the first subset of annotations is associated with the set of abnormal findings and wherein the second subset of annotations is associated with the set of normal findings.

11. The method of claim 9, wherein the set of radiology images is associated with a patient, the method further comprising, contemporaneously with displaying the set of radiology images, displaying a second set of radiology images associated with the patient, wherein the second set of radiology images is recorded prior to the set of radiology images.

12. The method of claim 11, wherein each of the second set of radiology images is linked with a corresponding image of the set of radiology images, wherein scrolling between images of the set of radiology images triggers a scrolling between corresponding images of the second set of radiology images.

13. The method of claim 12, further comprising, in the event that the user hovers the cursor proximal to the annotation of the second subset of annotations, displaying a corresponding annotation associated with the second set of radiology images.

14. The method of claim 9, further comprising preprocessing any or all of the set of radiology images, wherein preprocessing any or all of the set of radiology images comprises rotating one or more images.

15. The method of claim 9, further comprising automatically filling in a findings section of a radiologist report based on the set of image overlays.

16. The method of claim 9, wherein the set of radiology images is received from a Radiology Information System (RIS).

* * * * *

UNITED STATES PATENT AND TRADEMARK OFFICE
CERTIFICATE OF CORRECTION

| | |
|---|---|
| PATENT NO. | : 11,610,667 B2 |
| APPLICATION NO. | : 16/688623 |
| DATED | : March 21, 2023 |
| INVENTOR(S) | : Doktor Gurson et al. |

It is certified that error appears in the above-identified patent and that said Letters Patent is hereby corrected as shown below:

On the Title Page

Column 1, (71) Applicant, Line 1, Delete "Al," and insert --AI,-- therefor

Signed and Sealed this
Sixteenth Day of May, 2023

Katherine Kelly Vidal
*Director of the United States Patent and Trademark Office*